United States Patent [19]
Baumgart et al.

[11] Patent Number: 5,976,138
[45] Date of Patent: Nov. 2, 1999

[54] DISTRACTION SYSTEM FOR LONG BONES

[76] Inventors: Rainer Baumgart, Schieggstrasse 26, 81470 München; Augustin Betz, Am Sonnengrund 4a, 82319 Starnsberg, both of Germany

[21] Appl. No.: 09/030,066

[22] Filed: Feb. 25, 1998

[30] Foreign Application Priority Data

Feb. 28, 1997 [DE] Germany .......... 197 08 279

[51] Int. Cl.⁶ .................................................. A61B 17/56
[52] U.S. Cl. .................. 606/62; 606/63; 606/105
[58] Field of Search ................ 606/62–64, 67, 606/68, 105

[56] References Cited

U.S. PATENT DOCUMENTS 5,074,882  12/1991  Grammont et al. ............... 606/63

FOREIGN PATENT DOCUMENTS 0432253   6/1991   European Pat. Off. .
3921972   6/1994   Germany .
19527822  12/1996  Germany .

Primary Examiner—Michael Buiz
Assistant Examiner—Julian W. Woo
Attorney, Agent, or Firm—Rothwell, Figg, Ernst & Kurz, p.c.

[57] ABSTRACT

The distraction system for long bones includes a guide socket (42) and an intramedullary pin (10). It will make possible, in addition to elongation, also a segmental dislocation, as well as a segmental dislocation in combination with an elongation without repeated surgical intervention, while assuring a sufficient pressure on the bone contact surfaces of the docking site. Intramedullary pin (10) is thus provided on its outside wall with a projection (41) which engages in a longitudinal hole (43) in guide socket (42), whereby intramedullary pin (10) is secured against rotation by means of guide socket (42) attached in the long bone, but can be displaced axially.

4 Claims, 3 Drawing Sheets

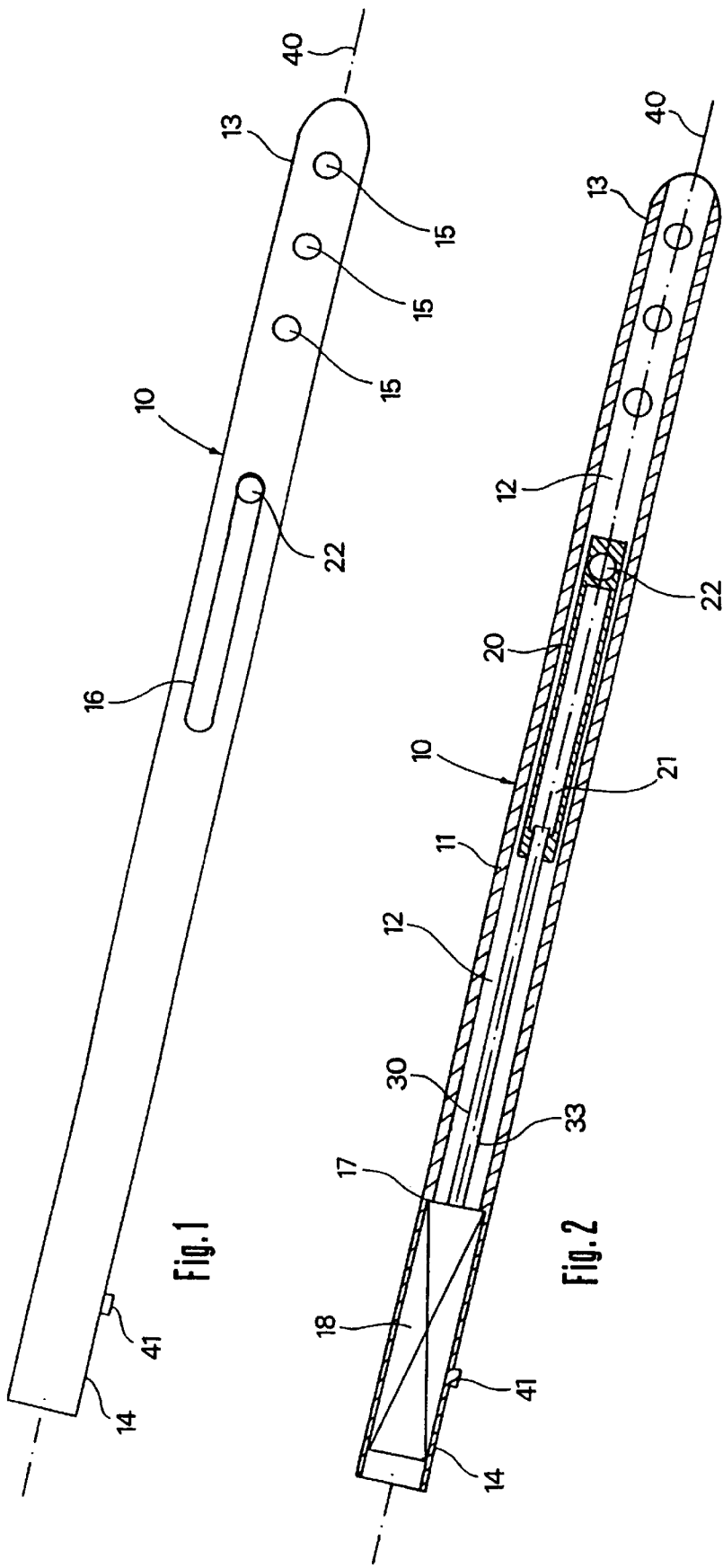

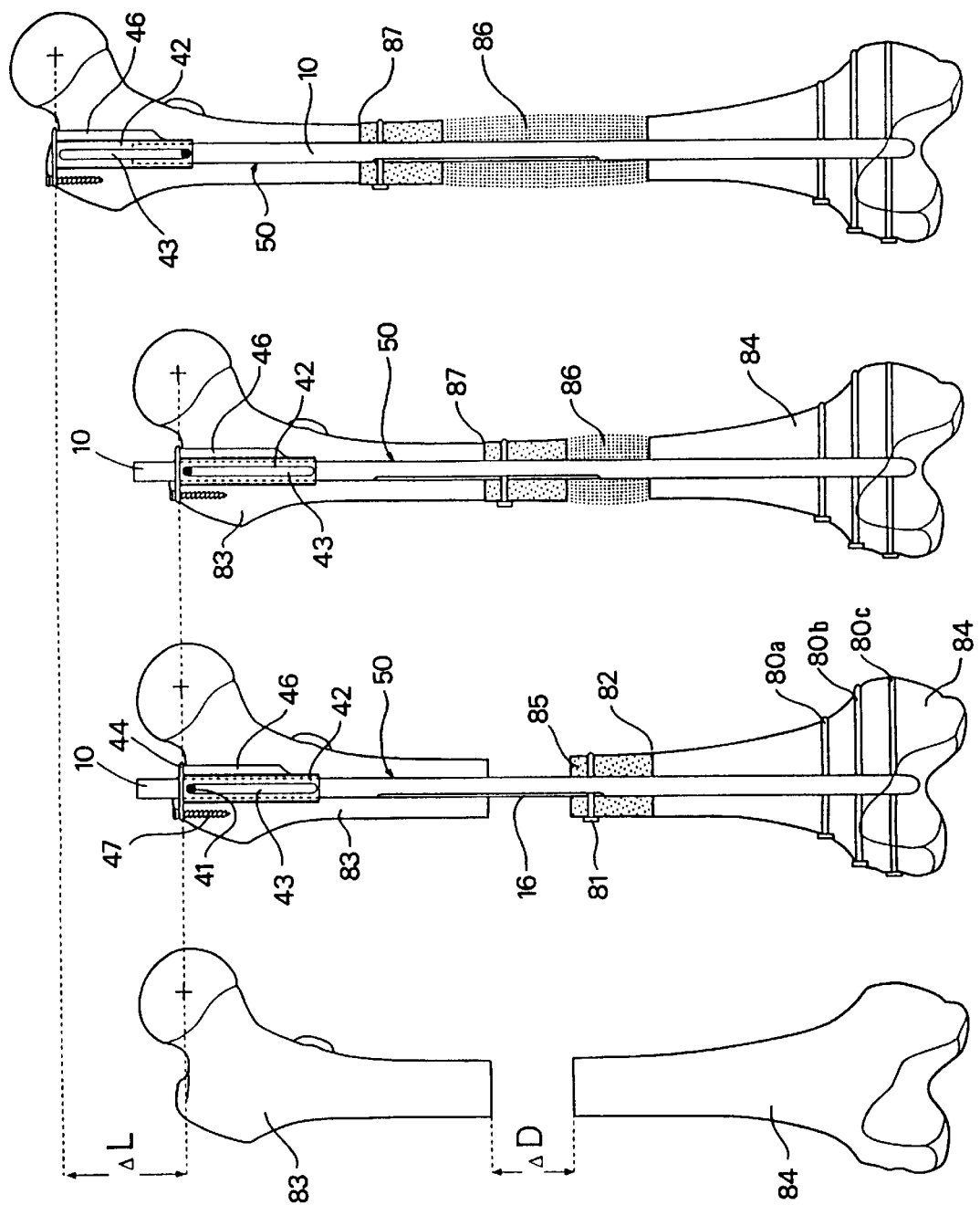

DISTRACTION SYSTEM FOR LONG BONES

BACKGROUND OF THE INVENTION

The invention concerns a distraction system for long bones with an intramedullary pin, which has a wall bounding a hollow space, with a distal end and a proximal drive-in end, and with a guide socket enclosing the proximal drive-in end of the intramedullary pin in the sliding seat, whereby the intramedullary pin has an inner part arranged in a longitudinally displaceable manner in the hollow space, in which a coaxial borehole with an internal thread is extended proceeding from its front side turned toward the proximal drive-in end, an abutment provided in the hollow space at a distance from the drive-in end, a rod having an outer thread, which engages as a screw with the inner thread of the borehole of the inner part, and which is coupled to a rotating drive lying on the abutment and arranged inside the hollow space, attachment holes for passage of distal attachment bolts arranged at a distance passing through the wall crosswise in the region of its distal end, a distal longitudinal hole [or holes] parallel to the longitudinal extension of the intramedullary pin arranged distally to the abutment and passing crosswise through the wall bounding the hollow space, if necessary on opposite-lying sides, and at least one attachment hole aligned flush with the longitudinal hole in the wall bounding the hollow space and passing crosswise through the inner part for passage a proximal attachment bolt.

The intramedullary pin utilized in this arrangement is known from EP 0 432,253 A1 and DE 3,921,972 C2. Bone elongations and segmental dislocations are possible according to the callus distraction method with this intramedullary pin. By application of integrated drives, the entire intramedullary pin can be implanted and can operate without material connection to the outside, which considerably reduces the risk of infection. As a rule, two longitudinal holes lying opposite one another or attachment holes lying opposite each other in pairs are provided in the wall of the intramedullary pin. With the use of intramedullary pins with wall open in their longitudinal direction, however, one longitudinal attachment hole or one attachment hole in the wall can suffice, since the wall is open on the opposite-lying side. Elongations of the femur of up to 10 cm also in combination with axial corrections can be successfully conducted with the intramedullary pin in the above-described configuration.

Indications for segmental dislocations exist when large bone defects are present of approximately 2 to 3 cm and more, such as may arise, e.g., directly as primary bone loss after impact situations, but also as secondary bone loss following infection or necrosis. Further, successful operations in the case of malignant bone tumors leave behind large bone defects.

If the known intramedullary pin is applied to segmental dislocation, an additional locking of the primary proximal fragment must be provided, so that the leg does not twist or become shortened. Frequently, the situation also exists where a shortening has already occurred, so that the defect may in fact be bridged with the segmental dislocation, but in addition to the segmental dislocation, another elongation of the extremity associated with this is also necessary.

In order to separately secure the proximal bone segment against axial dislocation in the case of a segmental dislocation, U-shaped notches are formed in the intramedullary pin according to DE 3,921,972 C2 in the region of its proximal end, and the legs of the U run parallel to the axis and the bottom combining segments are turned toward the drive-in end. Lamellae are formed by the U-shaped notches. A socket-shaped wedge element with outer wedges is guided in the proximal end of the intramedullary pin, and this element is axially displaced by rotating a screw held in threaded engagement by insertion at the drive-in end, and spreads apart the lamellae into a wedged position by its outer wedges, whereby a form fit with the proximal long bone and thus its secure positioning is achieved.

This design serves for the axial and rotational stabilization of the primary proximal bone fragment, as is necessary for segmental dislocation. A segmental dislocation in combination with an elongation, however, is not possible with this configuration. In addition, the later removal of the intramedullary pin is made difficult due to the spreading apart of the lamellae.

It has further been shown that a growing together of the dislocated segment and the primary fragment at the place of contact, which is also designated the docking site, is problematical at the end of segmental dislocation. The relatively reaction-poor front surfaces also have the tendency to bridge over under compression, so that for the most part additional compressive osteosyntheses or even an operative intervention and the addition of cancellous bone, for the most part from the pelvic crest, become necessary.

The arrangement of a guiding socket in the sliding seat around the proximal drive-in end of the intramedullary pin is already known from the literature citation Baumgart R., Betz A., Kettler M., Zeiler C., Schweiberer L.: Perspectives of Callus Distraction, Unfallchirurg 99, 84–91, 1996 [in German]. The objective of the arrangement of the guide socket primarily consists of a stabilizing effect, if the intramedullary pin migrates far into the bone at the end of treatment, since in this position, high tension peaks would otherwise be expected at its proximal end. The greater trochanter is inserted into the proximal force uptake component with the guide socket, whereby the danger of a loosening of the intramedullary pin or a proximal fracture of the femur is reduced.

The guide socket also essentially contributes to the simplification of the removal of the intramedullary pin, since in the case of intramedullary pins that have penetrated far into the medullary space, at the end of the distraction in the case of large elongation segments, the finding of the end of the intramedullary pin and the placement of the extraction instruments may present difficulties.

The guide socket itself is held laterally in the greater trochanter by means of an overlaying strap with an opening, through which the attachment means to the long bone, for example, a screw, can be introduced, so that the position of the guide sleeve is secured both axially as well as in a rotational manner. The axial securing against displacement is necessary in any case, because both a sliding distally into the medullary space, as well as particularly a sliding out proximally from the medullary space represent disadvantages and lead to a loss of function.

The use of such a distraction system is limited to elongations of the long bone; segmental dislocations and combinations of segmental dislocations and elongations cannot be conducted.

An intramedullary pin is known from DE 195-27,822 C1 for the rigid combining of parts of a bone. The intramedullary pin has a sheath that can be attached to one bone part and a rotatable socket can be taken up in this sheath. The rotatable socket can be joined with another bone part by means of a longitudinal guide introduced into the sheath. The rotatable socket engages in form-fitting manner on a threaded spindle. The threaded spindle is joined with a transport element, which can be connected with another bone segment arranged between two bone parts that is separated from a fracture end. The transport element can be moved in translation along the longitudinal axis in the sheath by rotating the rotatable socket. The attachment of the bone segment separated from one fracture end is made by means of a bone screw, which is guided in the sheath by means of a longitudinal guide. The two bone parts are thus joined with the sheath by means of bone screws and are joined in the pre-given operative position. This means that the shortened bone can be stabilized only intraoperatively in the original length. The structure of the intramedullary pin permits limited radial angular movements of the distal bone part, which are converted into an axial movement of the transport element by means of a toothed gearing with directional blocking and the threaded spindle, and this motion in turn displaces the bone segment in the defect between the bone parts. Only a segmental dislocation can be achieved with the known intramedullary pin. A bone elongation as well as a combination of segmental dislocation and elongation according to the callus distraction method is not possible.

SUMMARY OF THE INVENTION

The task that is the basis of the invention consists of configuring the distraction system of the above-given type, so that in addition to the lengthening, a segmental dislocation as well as both a segmental dislocation in combination with an elongation are possible without repeated operations, whereby a sufficient pressure of the bone contact surfaces will be produced at the docking site without extra surgical intervention.

Proceeding from the distraction system of the type named initially, this task is resolved by at least one projection projecting from the wall of the intramedullary pin and by means of at least one longitudinal hole formed in the guide socket parallel to its axis, and this hole is engaged in a guiding manner with the projection without projecting beyond the outer wall of the guide socket.

The stability of the guide socket against rotation can be improved still further by the fact that on its outer side, at least one longitudinal rib formed in a knife shape is provided parallel to its axis, and this rib advantageously extends distally from its proximal end.

The guide socket prevents a shortening from occurring in the case of segmental dislocations and causes the fact that the primary proximal fragment is joined with the primary distal fragment and thus with the lower leg in a rotation-stable manner. Both tasks are undertaken by a projection or even better, by two projections lying opposite one another on the periphery, each engaged with a correspondingly arranged longitudinal hole. The rotational stability is given only by the fact that the primary distal fragment is joined with the intramedullary pin resistant to rotation by distal locking bolts, the intramedullary pin is joined with the guide socket in a rotation-resistant manner by means of these one or more projections via the longitudinal hole, and the guide socket is joined with the primary proximal fragment in a rotation-resistant manner by the lateral overlying strap and the screw in the opening. The position of the projections is the proximal longitudinal hole boundary at the beginning of the distraction treatment at the end of the operation, by means of which a shortening of the extremity due to muscle pull will be prevented.

Additional rotational stability is supplied by the sword-shaped longitudinal rib arranged at the medial circumference, which is driven into the compact cancellous bone in the vicinity of the solid bone.

The guide socket also effects a compression of the front surfaces at the docking site without repeated operation by the further acting drive alone during the elongation phase and in this way stimulates spontaneous restructuring. Another osteosynthesis for compression of the contact places or a molding of cancellous bone, thus an addition of bone (usually from the pelvic crest), can be avoided.

If the bone defect requires only a segmental dislocation, the guide socket only takes on the task of rotational stabilizing. The projection or projections remain positioned at the proximal end of the longitudinal hole and secure the length of the extremity during the entire treatment. The intramedullary pin usually stands at a proximal distance of approximately 2 cm over the upper edge of the trochanter or is flush with this edge. Distally, locking is produced in the primary fragment, as is usual also in the case of elongation. Approximately 3 cm distal to the proximal front surface of the primary distal fragment, a careful tissue corticotomy is produced. The locking of the mobilized bone segment with an attachment bolt is produced at the distal end of the longitudinal hole in the intramedullary pin. At the end of the segmental dislocation, upon reaching the docking site, the dislocation segment is pressed by its proximal front surface to the distal front surface of the primary proximal fragment. With sufficient compressive pressure, propulsion is stopped, the regenerated bone is reinforced, and the docking site is bridged.

For a partial seal of the at-least one longitudinal hole in the guide socket, a wall element can be inserted into this socket in its distal region in a form-fitting manner. The wall element forms an extension of the inside or outside wall of the guide socket and is held by means of a slight undercut. A possible undesired elongation, which could be caused by traction of the actuation required for the compressive pressure is avoided by the use of such an undercut in the length corresponding to the dimensioned wall element, when the displacement element has reached the docking site, in that the proximal front side of the wall element acts as a stop for the projection of the intramedullary pin. In this configuration, the guide sockets are each produced with longitudinal holes of the same maximum length. Adaptation to the desired working length of the longitudinal hole corresponding to the required extent of elongation is then produced by inserting the wall element dimensioned corresponding in length into the longitudinal hole of the guide socket.

If a bone defect associated with a shortening of the extremity is present, then introducing the intramedullary pin and the segmental dislocation is produced in the same way, as in the case of a bone defect alone. When the docking site is reached, however, the actuation is not stopped, but pulls further in an unchanged manner, so that now the elongation process begins automatically without repeated operation. If lengthwise equilibration is reached, the propulsion is stopped and the regenerated bone is reinforced.

For dimensioning the longitudinal holes in the intramedullary pin and in the guide socket, care is to be taken that the longitudinal hole in the guide socket is required only for elongation and elongation is limited, while the longitudinal hole in the intramedullary pin must be dimensioned both for the segmental dislocation as well as for the elongation. For a segmental dislocation of 3 cm, for example, and an elongation of 5 cm, a longitudinal hole of 5 cm in the guide socket is required, whereas the length of the longitudinal hole must amount to 8 cm in the intramedullary pin, whereby the diameter of the guide bolt, which usually corresponds to the width of the longitudinal hole must be added to these indicated values for the longitudinal holes.

BRIEF DESCRIPTION OF THE DRAWINGS

Examples of embodiment of the invention will be explained in more detail based on the drawings. Here:

FIG. 1 shows in a side view an intramedullary pin for the distraction system according to the invention;

FIG. 2 shows a longitudinal section of the intramedullary pin of FIG. 1;

FIG. 5 shows schematically a bone with a defect site and a shortening;

FIG. 6 shows schematically the bone of FIG. 5 with the applied distraction system;

FIG. 7 shows, in a view like FIG. 6, the end of the segmental dislocation; and

FIG. 8 shows, in a view like FIG. 7, the end of the bone elongation adjacent to the segmental dislocation.

DETAILED DESCRIPTION OF THE INVENTION

Figure 3:
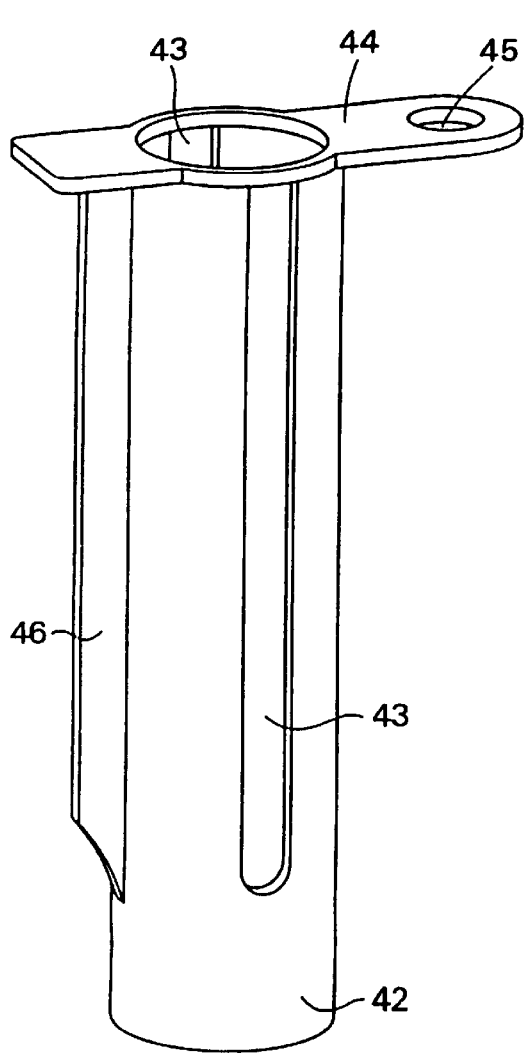
FIG. 3 shows perspectively the guide socket of the distraction system.

Intramedullary pin 10 shown in FIGS. 1 and 2 corresponds in its structure to [that of] DE 3,921,972 (FIGS. 1 and 2). Intramedullary pin 10 has a distal end 13 and a proximal end 14 as well as a wall 11, which essentially has the form of a cylinder with an axis 40. Three attachment holes 15 extending perpendicularly to axis 40 and arranged in wall 11 in the region of the distal end and used for passage of distal attachment bolts 80a, 80b, 80c (FIG. 6) are provided. An inner part 20 is arranged inside wall 11 of intramedullary pin 10, and this part, proceeding from its proximal front surface, has a borehole 21 with an inner thread, with which a rod 30 with an outer thread 33 is connected coaxially in a screw engagement. Rod 30 is coupled at its free end with a rotational actuator 18, which in turn is applied onto an abutment 17 on the inside of wall 11. Perpendicular to axis 40, an attachment hole 22 extends through inner part 20, and two longitudinal holes 16 that are axis-parallel and lie opposite each other flush to this hole are aligned in wall 11 for passage of a proximal attachment bolt 81, but only one of these [holes] can be seen from the representation shown in FIGS. 6 to 8.

If the bone between attachment holes 15 and attachment hole 22 is separated, by rotating rod 30 via actuator 18 attached to the abutment and by the thread engagement between rod 30 and central borehole 21 in inside part 20, the edges of osteotomy 82 (FIG. 6) are gradually distanced from each other, whereby the widening gap is filled with newly formed bone tissue 86 (FIG. 7).

Figure 4:
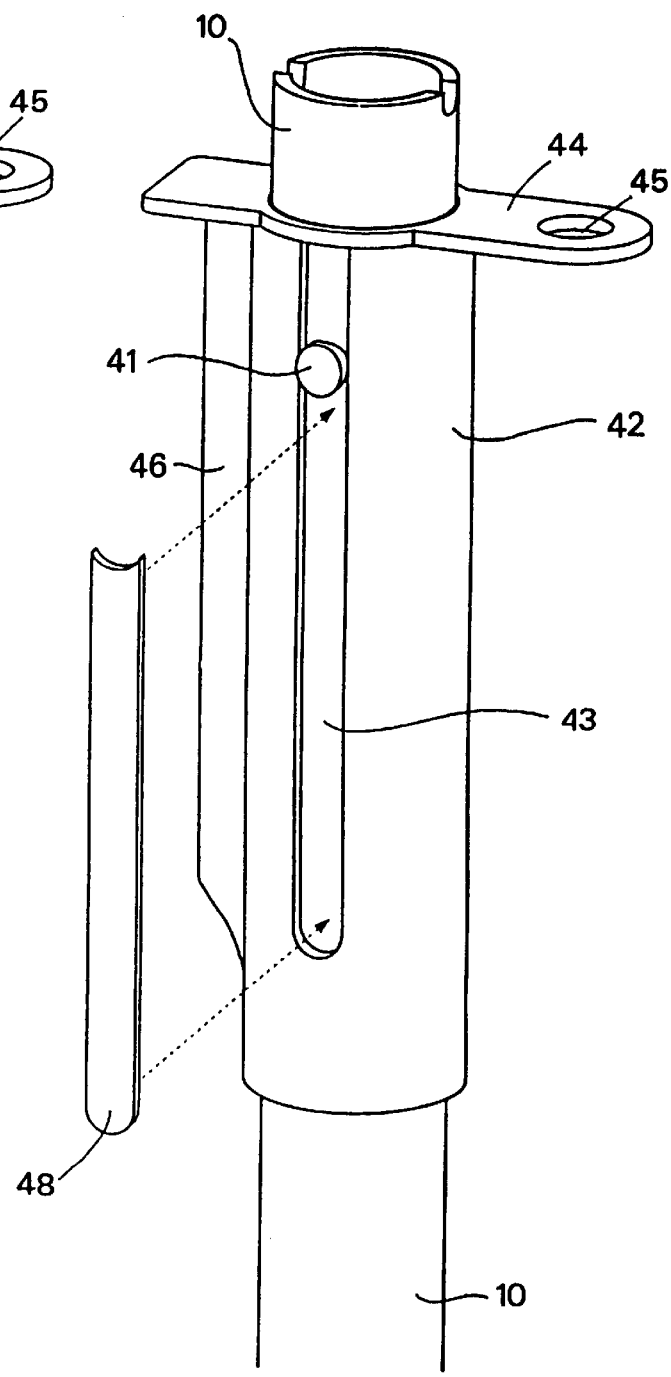
FIG. 4 shows perspectively the proximal end of the distraction system comprised of a guide socket and an intramedullary pin.

In the case of the distraction system, intramedullary pin 10 is provided with a projection 41 in the region of its proximal drive-in end 14. As can be seen in FIGS. 3 and 4, a guide socket 42 is part of this distraction system, and this socket has an axis-parallel longitudinal hole 43 proceeding from its proximal end, and projection 41 of intramedullary pin 10 engages in this hole. As can be seen from FIG. 4, two longitudinal holes 43 lying opposite one another are provided. In this configuration of the distraction system, two projections 41 lying opposite one another on the periphery are formed in the region of the proximal drive-in end 14 of intramedullary pin 10. Guide socket 42 has on the proximal end a strap 44 overlying both sides laterally, in which an opening 45 is formed on one side for passage of a fastening means (not shown). On the side lying opposite opening 45, a sword-shaped longitudinal rib 46 is formed at the periphery of guide socket 42, and this rib extends in an axis-parallel manner and radially outwardly beneath a lateral projection of strap 44. Intramedullary pin 10 sits in guide socket 42 in the sliding seat, whereby projections 41 do not project over the contour of the outer wall of guide socket 42 and prevent by their engagement in longitudinal holes 43 a distortion [twisting] between intramedullary pin 10 and guide socket 42.

As can be seen from FIG. 5, the bone that is depicted has a primary proximal fragment 83 and a primary distal fragment 84, which are separated from one another by a defect site at a distance of ΔD. The bone is also shortened by length ΔL.

As can be seen from FIG. 6, a flush borehole 50 is shaped in the two primary fragments 83 and 84. The distraction system comprised of a guide socket 42 and an intramedullary pin 10 that can be axially displaced in it, is introduced into borehole 50 in primary proximal fragment 83. Guide socket 42 is held secure against distortion and axially attached in primary proximal fragment 83, on the one hand, by a screw 47 guided through opening 45 (FIG. 4) in strap 44 and, on the other hand, by the sword-shaped longitudinal rib 46, which is driven into the primary proximal fragment 83. By engagement of projections 41 in longitudinal holes 43, intramedullary pin 10 is held, however, in a way that is limited in its axial motion, and securely against twisting relative to guide socket 42.

A wall element 48 partially closing longitudinal hole 43 can be inserted in a form-fitting manner into longitudinal hole 43 of guide socket 42, in its distal region, whereby the distal front surface of wall element 48 lies at the distal end surface of longitudinal hole 43. The outer or inner wall essentially corresponds to the contour of the outer or inner wall of guide socket 42, whereby a slight undercut can be provided in longitudinal hole 43 for holding wall element 48. Due to the fact that after a pre-given dislocation path, projection 41 of intramedullary pin 10 stops at the distal front surface of wall element 48, the displacement of intramedullary pin 10 distally is limited to a pre-given length, which is smaller than that of longitudinal hole 43.

Attachment bolts 80a, 80b and 80c are guided through attachment holes 15 (FIGS. 1 and 2), as shown in FIG. 6, and anchored in primary distal fragment 84. Further, an attachment bolt 81 is passed through longitudinal holes 16 in wall 11 of the intramedullary pin and through attachment hole 22 in inner part 20, and anchored in displacement element 85.

After conducting the corticotomy or osteotomy 82 distally from guide bolt 81, drive 18 (FIG. 2) is activated, whereby the displacement segment 85 formed proximally to corticotomy 82 is moved in the direction of docking site 87 of primary proximal fragment 83 according to the callus distraction method with the formation of regenerated bone 86, whereby defect site ΔD is eliminated. By further running drive 18, a relatively high pressure is exercised at docking site 87, and this pressure promotes the growing together of the displacement segment 85 with the proximal primary fragment 83.

As can be seen from FIG. 8, without further surgical intervention, a bone elongation by length ΔL can be produced according to the callus distraction method by further moving drive 18 (FIG. 2), whereby intramedullary pin 10 migrates inside guide socket 42, whose length is dimensioned such that a tip-free positional stability remains assured.

By attaching intramedullary pin 10 by means of guide bolts 80*a*, 80*b* and 80*c* in primary distal fragment 84 and by means of guide bolt 81 proximal to guide bolts 80*a*, 80*b*, 80*c*, by the formation of the corticotomy or osteotomy 82 distal to guide bolt 81 and by attaching intramedullary pin 10 via guide socket 42 in a rotation-resistant manner and thus relative to primary proximal fragment 83, the exact alignment of primary fragments 83 and 84 (including displacement segment 85) relative to one another remains assured both during the closing of the defect site as well as during the bone distraction.

We claim:

1. Distraction system for a long bone having an intramedullary pin, which has a wall bounding a hollow space, with a distal end and a proximal drive-in end, and a guide socket surrounding the proximal drive-in end of intramedullary pin in sliding seat, whereby the intramedullary pin (a) has an inner part arranged in a longitudinally displaceable manner in said hollow space, in which, proceeding from its front side turned toward its proximal drive-in end, a coaxial borehole with an inner thread extends;

(b) an abutment is provided in said hollow space at a distance from the drive-in end;

(c) a rod is provided, which has an outer thread, which has a screw engagement with the inner thread of said borehole of the inner part, and which is coupled with a rotational drive lying on the abutment and arranged inside the hollow space;

(d) attachment holes are provided for passage of distal attachment bolts, arranged at a distance and passing crosswise through the wall in a region of the distal end;

(e) at least one longitudinal hole is provided parallel to the longitudinal extension of intramedullary pin and passing crosswise through the wall bounding the hollow space and arranged distally from the abutment; and (f) at least one attachment hole is provided for passage of a proximal attachment bolt aligned flush relative to the longitudinal hole in the wall bounding the hollow space and passing crosswise through the inner part;

wherein at least one projection is projecting from the wall of the intramedullary pin and at least one longitudinal hole is parallel to its axis and formed in the guide socket, which is engaged with the projection as a guide without projecting over an outer wall of the guide socket.

2. Distraction system according to claim 1, wherein the guide socket has on its outer side at least one longitudinal rib parallel to its axis.

3. Distraction system according to claim 2, wherein the longitudinal rib extends from the proximal drive-in end of the guide socket.

4. Distraction system according to claim 1, wherein the wall includes a wall element which can be inserted in a form-fitting manner in a distal region of the at-least one longitudinal hole in the guide socket for its partial closure, without projecting inside and outside over a wall contour of the guide socket.

* * * * *